United States Patent
Lu et al.

(10) Patent No.: US 10,213,606 B2
(45) Date of Patent: *Feb. 26, 2019

(54) MODULATE PACING RATE TO INCREASE THE PERCENTAGE OF EFFECTIVE VENTRICULAR CAPTURE DURING ATRIAL FIBRILLATION

(71) Applicant: Medtronic, Inc., Minneapolis, MN (US)

(72) Inventors: Richard M. T. Lu, Medina, MN (US); Subham Ghosh, Blaine, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 723 days.

This patent is subject to a terminal disclaimer.

(21) Appl. No.: 14/211,884

(22) Filed: Mar. 14, 2014

(65) Prior Publication Data

US 2014/0277245 A1    Sep. 18, 2014

Related U.S. Application Data

(60) Provisional application No. 61/798,303, filed on Mar. 15, 2013.

(51) Int. Cl.
*A61N 1/37* (2006.01)
*A61B 5/046* (2006.01)
(Continued)

(52) U.S. Cl.
CPC .............. *A61N 1/371* (2013.01); *A61B 5/046* (2013.01); *A61N 1/3624* (2013.01);
(Continued)

(58) Field of Classification Search
CPC .... A61N 1/371; A61N 1/3624; A61N 1/3716; A61N 1/3684; A61N 1/3622; A61B 5/046
See application file for complete search history.

(56) References Cited

U.S. PATENT DOCUMENTS 5,999,850 A * 12/1999 Dawson ............... A61N 1/3622
607/4
7,187,972 B1    3/2007 Fain et al.
(Continued)

FOREIGN PATENT DOCUMENTS

EP    1110580 A2    6/2001

OTHER PUBLICATIONS (PCT/US2014/028108) PCT Notification of Transmittal of the International Search Report and the Written Opinion of the International Searching Authority.

*Primary Examiner* — Rex R Holmes

(57) ABSTRACT

The present disclosure pertains to cardiac pacing methods and systems, and, more particularly, to cardiac resynchronization therapy (CRT). In particular, the present disclosure pertains to determining whether a patient is experiencing atrial fibrillation (AF). If the patient is experiencing AF, the efficacy of CRT is determined. A signal is sensed in response to a ventricular pacing stimulus. Through signal processing, a number of features are parsed from the signal and a determination is made as to whether the ventricular pacing stimulus evoked a response from the ventricle.

26 Claims, 7 Drawing Sheets

(51) Int. Cl.
 *A61N 1/362* (2006.01)
 *A61N 1/368* (2006.01)
(52) U.S. Cl.
 CPC ......... *A61N 1/3684* (2013.01); *A61N 1/3716* (2013.01); *A61N 1/3622* (2013.01)

(56) References Cited

U.S. PATENT DOCUMENTS

| | | | |
|---|---|---|---|
| 2004/0215259 A1 | 10/2004 | Krig et al. | |
| 2011/0319951 A1* | 12/2011 | More ................... | A61N 1/368 607/14 |
| 2012/0165897 A1* | 6/2012 | Enrooth ................ | A61N 1/371 607/28 |

* cited by examiner

MODULATE PACING RATE TO INCREASE THE PERCENTAGE OF EFFECTIVE VENTRICULAR CAPTURE DURING ATRIAL FIBRILLATION

RELATED APPLICATION

This application claims the benefit of U.S. Provisional Application No. 61/798,303, filed on Mar. 15, 2013, now lapsed.

CROSS-REFERENCE TO RELATED APPLICATION

Cross-reference is hereby made to the pending commonly-assigned related U.S. Application, entitled MODULATE PACING RATE TO INCREASE THE PERCENTAGE OF EFFECTIVE VENTRICULAR CAPTURE DURING ATRIAL FIBRILLATION, U.S. application Ser. No. 14/212,025 to Lu et al., filed concurrently herewith and incorporated herein by reference in its entirety.

FIELD

The present disclosure pertains to cardiac pacing methods and systems, and, more particularly, to cardiac resynchronization therapy (CRT).

BACKGROUND

Cardiac resynchronization therapy devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle.

For a variety of reasons, cardiac pacing systems may not effectively capture a ventricle. For example, a patient experiencing atrial fibrillation (AF) may have an implantable cardioverter-defibrillator (ICD) that shows a very high percentage (e.g., greater than 90%) of delivered biventricular (BiV) paces compared to sensing of intrinsic activations. However, BiV pacing may be ineffective if the paces are delivered to myocardial tissue in a refractory state (i.e. subnormal excitability of myocardial tissue following excitation), resulting in pseudo-fusion. Pseudo-fusion involves electrical activation of ventricles almost entirely through intrinsic electrical activity with minimal or no contribution from pacing of the ventricle(s). Pseudo-fusion can occur during AF, because AF results in irregular conduction of atrial impulses to the ventricles. In turn, irregular ventricular activation rate increases the chance of inconsistent capture of the ventricles. Typically, delivery of substantially consistent BiV pacing during AF is achieved by overdriving the ventricular intrinsic rate. However, overdriving ventricular rate can lead to unfavorable cardiac mechanics and can exacerbate heart failure. Therefore, it is desirable to increase the percent of effective BiV pacing during AF without significantly increasing the ventricular rate.

DETAILED DESCRIPTION OF EXEMPLARY EMBODIMENTS

Figure 1:
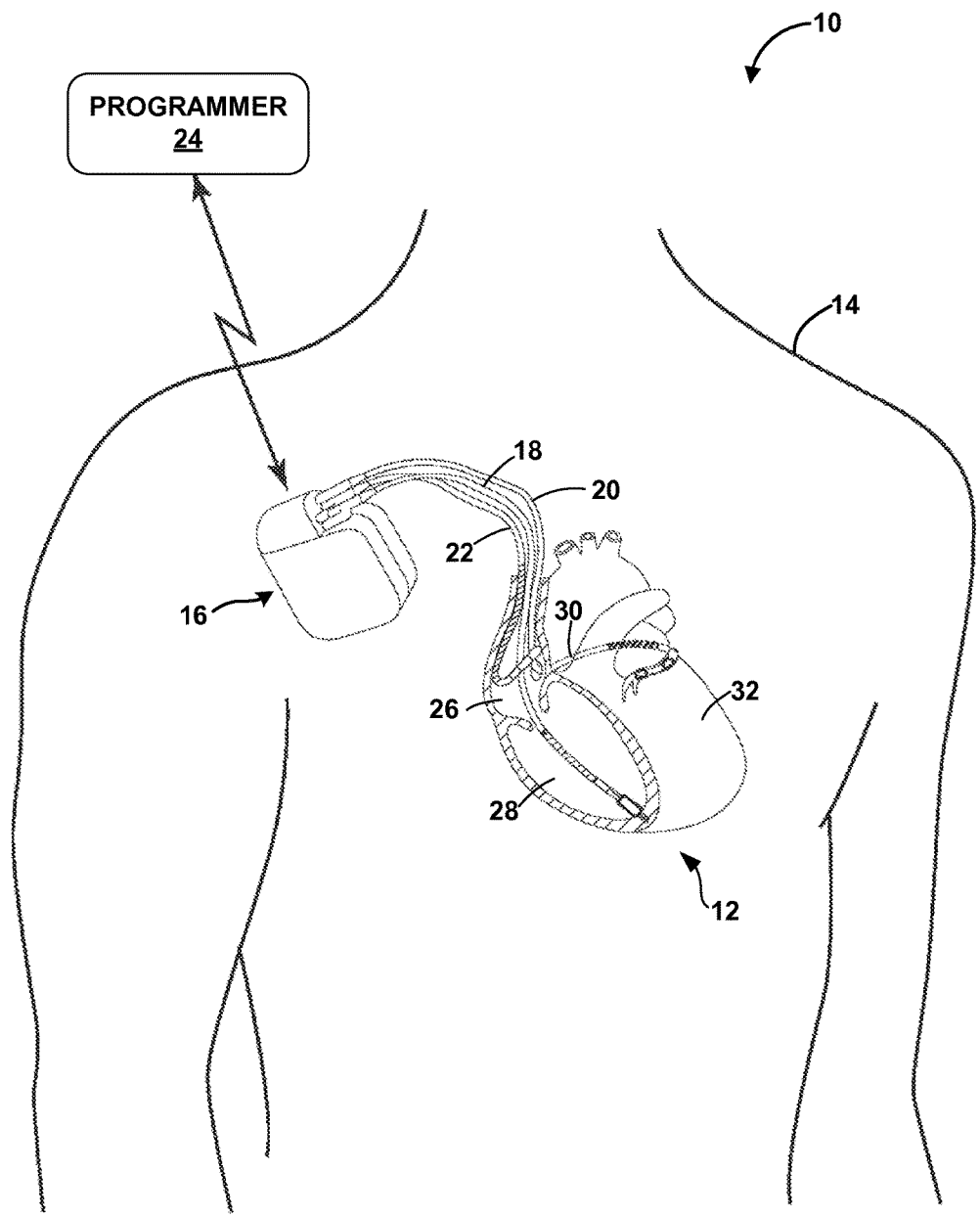
FIG. 1 is a diagram of an exemplary system including an exemplary implantable medical device (IMD).

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

One or more embodiments of the present disclosure are directed to an implantable medical device (IMD) configured to deliver bi-ventricular cardiac resynchronization therapy (CRT). The IMD (e.g. implantable cardioverter-defibrillator (ICD)) is configured to determine whether pacing stimuli effectively captures a ventricle during atrial fibrillation (AF). Determining whether the ventricular pacing stimulus is capturing the paced ventricle occurs solely during atrial fibrillation. Depending upon whether effective capture is achieved during AF, the heart rate target level may be incrementally adjusted. Exemplary incremental adjustments can be 1-5 beats per minute or 1 percent (%), 2%, 3%, 4%, %5 or 10% of the HR target level. The IMD can use a normal process mode of operation or a duty cycle mode of operation to adjust the target heart rate to increase effective capture during AF. Normal process mode generally entails the IMD continuously determining whether a pacing stimuli effectively captures a ventricle and adjusting the target rate during AF. In contrast, the duty cycle mode conserves power by not continuously determining whether the pacing stimuli effectively captures the ventricle during AF. For example, the duty cycle mode may operate 10% of the time over a period of time (e.g. daily, weekly, etc.). Alternatively, the duty-cycle mode of operation can be configured as a function of AF burden. For example, the duty cycle mode can operate a certain number of hours while AF is detected.

In yet another embodiment, a combination of the normal mode of operation and the duty cycle mode of operation can be employed. For example, a normal mode of operation can be used for the first N hours of AF per day where N is any number between 1 and 12 followed by a duty-cycle mode. In another embodiment, the feature as to determining effective capture is always run in a duty-cycle mode.

In either case, a fixed or adjustable duty-cycle mode of X % can be then employed by the IMD where X may be some function of the number of hours for which the patient is in AF. For example, in one or more preferred embodiments, duty-cycle mode of X % means that the feature, related to determining effective capture during AF and adjusting the target pacing rate in response, has the first 100 beats per hour are analyzed to determine statistical data on effective capture while the remaining portion of the hour and, every subsequent hour thereafter, performs duty cycling in a pre-specified manner (e.g. 10 seconds operation out of each 30 seconds).

In one or more other embodiments, duty-cycle mode of X % means that the feature, related to determining effective capture during AF and adjusting the target pacing rate in response, is activated for the first (X/100)*60 minutes of an hour. For example, an adjustable duty-cycle operation may run 100% for the first hour of AF, then duty-cycle may decrease in fixed decrements of 4% for each extra hour. The duty-cycle mode would be 96% for the second hour, 92% for the third hour, . . . 18% in the $24^{th}$ hour. For this particular example, the effective duty cycle for 24 hours of AF would be 54%.

In still yet another embodiment, the duty cycle mode can operate a predetermined percentage of time. For example, the duty cycle mode can operate 50% of a specified time period (e.g. 50% every minute etc.); therefore, the duty cycle mode would run every 0.5 minute.

In one or more preferred embodiments, upon activating the feature related to determining effective capture during AF and adjusting the target pacing rate in response, a non-duty cycle mode is configured to run for e.g. 30 seconds ("initialization period"). Thereafter, this feature would begin to operate in duty cycle mode.

The heart rate, measured at the end of the initialization period, is then adjusted or augmented to a final designated pacing rate by 1 beats per minute (BPM) if the heart rate is greater than 100 BPM, 3 BPM if the heart rate is greater than 80 BPM but less than 100 BPM, and 5 BPM if the heart rate is less than 80 BPM. The final designated pacing rate is then applied during a hold period of 30 seconds. The hold period begins after the initialization period ends, and ends 30 seconds later. During the hold period, the pacing rate can only be adjusted upward if a certain pre-specified number of sensed ventricular events are met out of the total number of ventricular events. For example, the pacing rate can only be adjusted upward if 6 of 10 ventricular events in any period of 10 ventricular events are sensed ventricular events, not paced ventricular events. If 6 of 10 ventricular events in any period of 10 ventricular events are sensed, the heart rate can be increased by 2 BPM and the buffer of 10 beats is cleared. Battery power is conserved because determination of sensed versus paced events is very simple compared to the determination of effective capture versus ineffective capture. At the end of the hold period, 10 beats are analyzed for effective capture. Depending on how many of the 10 beats have effective capture, the pacing rate for the next 30 second hold period is adjusted up or down.

The present disclosure achieves effective capture during AF by delivering pacing stimuli at sufficient energy and at the proper timing. Additionally, morphology analysis of paced electrograms is used to determine effective capture, which provides beneficial results over known capture management algorithms. While capture management algorithms are able to artificially modify the timing (i.e., overdrive pace or use very short SAV/PAV), the main focus of capture management algorithms is on sufficient energy delivery of a pacing stimulus. Capture management algorithms generally do not address proper timing and cannot be used to assess effective capture during normal device operation. Moreover, capture management algorithms generally do not optimally work during AF or fast heart rates.

Figure 2:
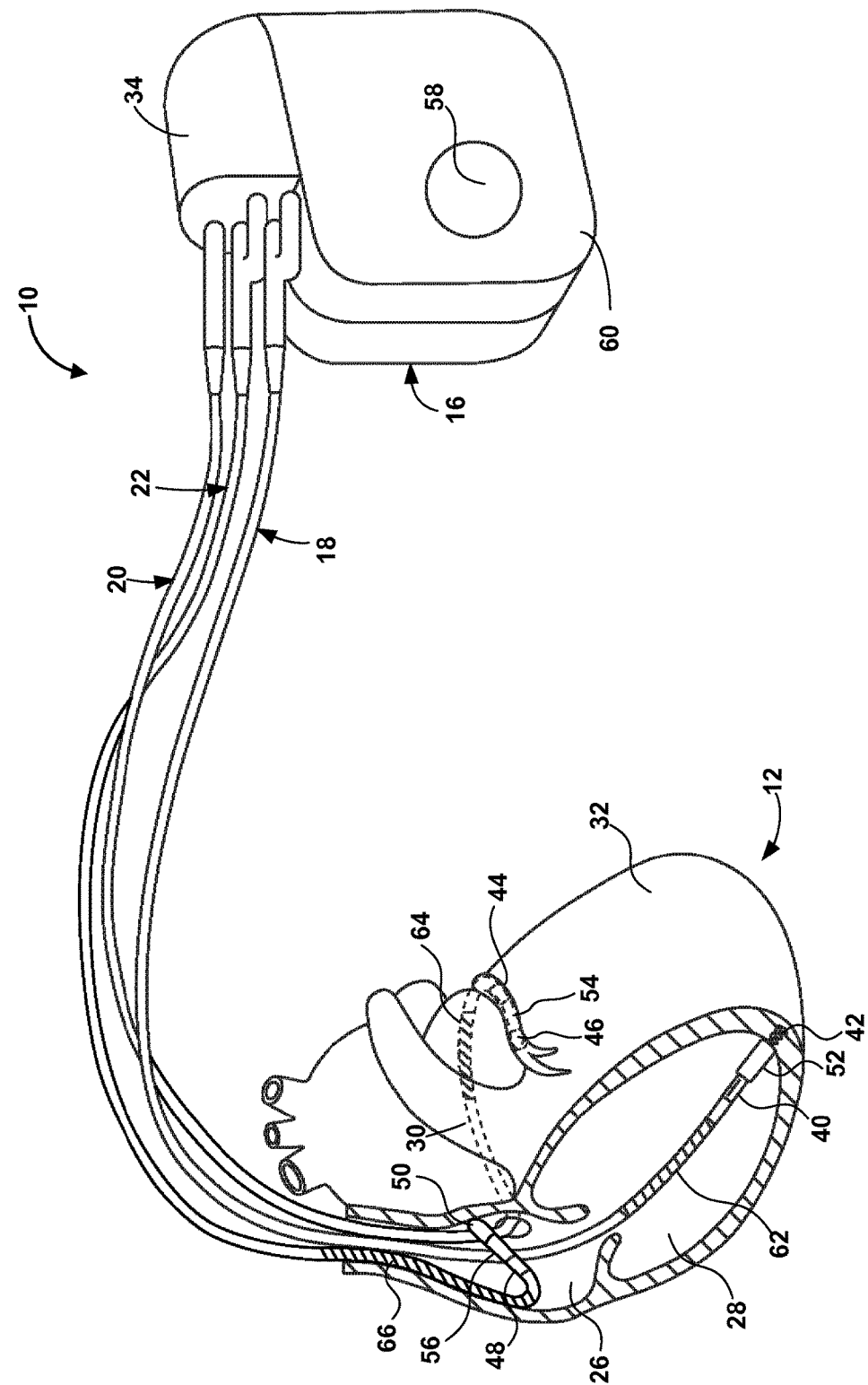
FIG. 2 is a diagram of the exemplary IMD of FIG. 1.

Presented below is a description of the IMD hardware (FIGS. 1-3). Thereafter, a description is presented of one or more processes (FIGS. 4-6) used for modulating the pacing rate in order to increase the percentage of effective ventricular capture during AF.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. Lead 22 is configured to acquire signals indicative of atrial fibrillation.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. patent application Ser. No. 13/717,896 filed Dec. 18, 2012, and assigned to the assignee of the present invention, the disclosure of which is incorporated by reference in its entirety herein as modified by preferably using a LVtip (i.e. electrode 46)-Rvcoil (i.e. electrode 62) for the pacing vector and the sensing vector, respectively. It is generally understood by those skilled in the art that other electrodes can also be selected as pacing and sensing vectors. Electrode 44 and 64 refer to the third and fourth LV electrodes in the claims.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

Figure 3A:
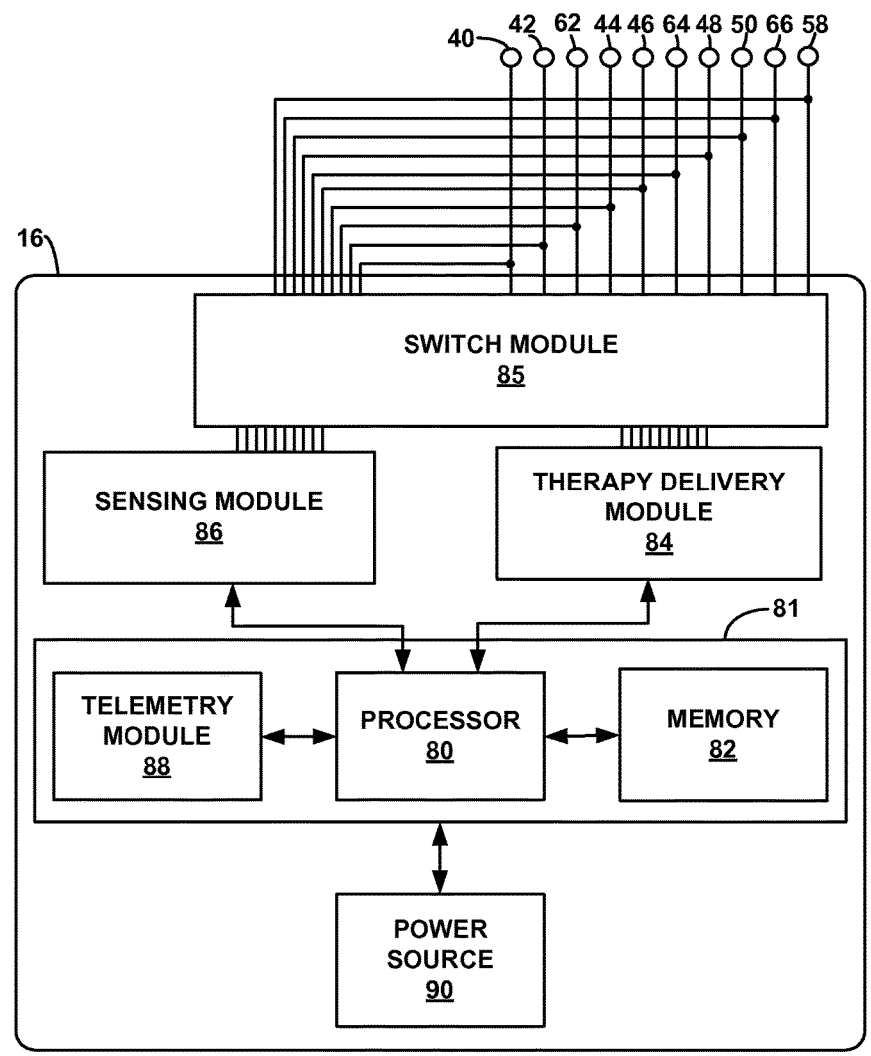
FIG. 3A is a block diagram of an exemplary IMD, e.g., the IMD of FIGS. 1-2.

FIG. 3A is a functional block diagram of one exemplary configuration of the IMD 16. As shown, the IMD 16 includes a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. Memory 82 includes computer instructions related to capture management. An exemplary capture management module such as left ventricular capture management (LVCM) is briefly described in U.S. Pat. No.

7,684,863, which is incorporated by reference in its entirety. As to the delivery of pacing stimuli, capture management algorithms typically focus on sufficient energy delivery of a pacing stimulus.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time. When a patient is experiencing AF, processor 80 is further configured to determine pacing effectiveness using a normal process mode or a duty cycle mode.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
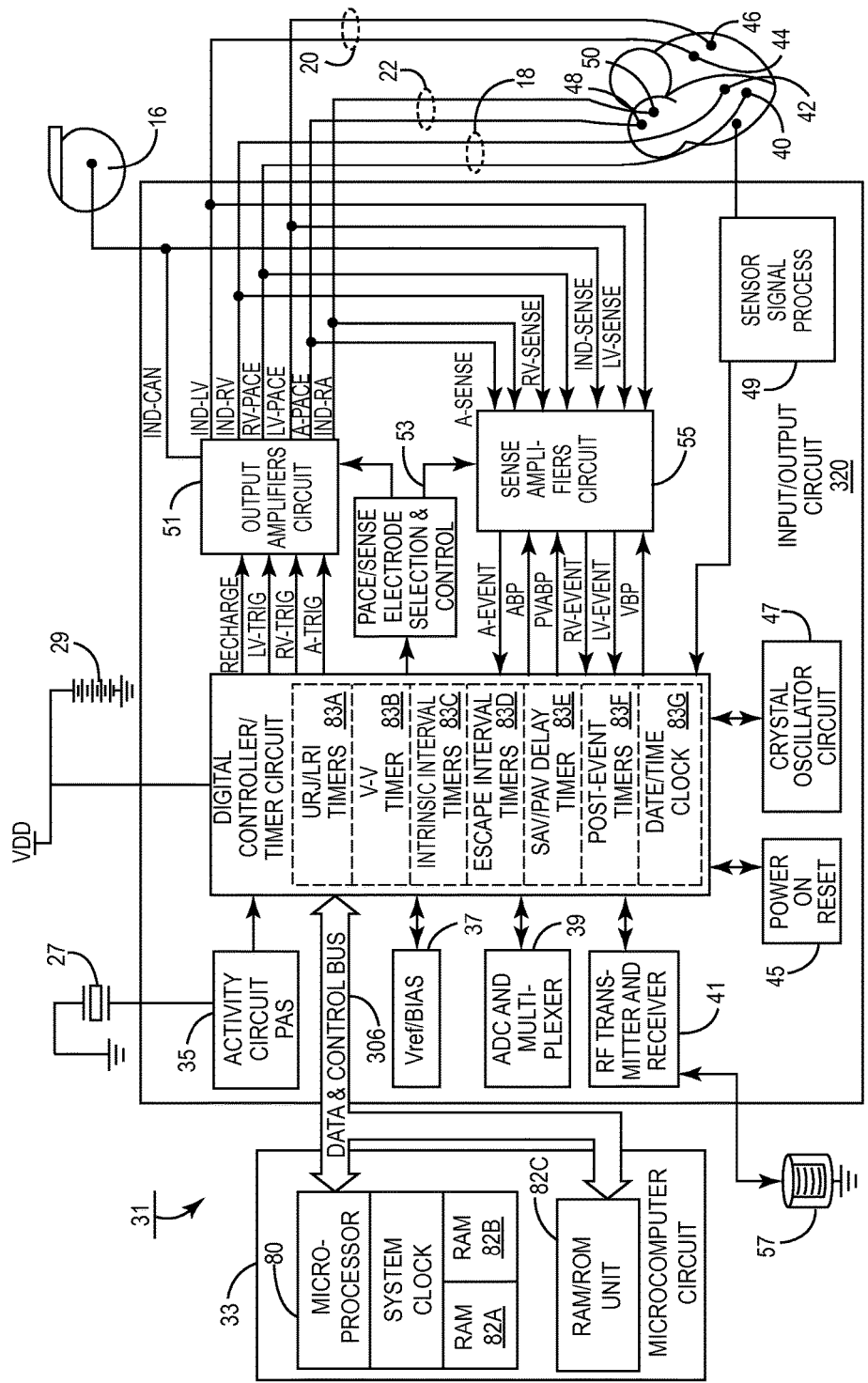
FIG. 3B is yet another block diagram of one embodiment of IMD (e.g. IPG) circuitry and associated leads employed in the system of FIG. 2 for providing three sensing channels and corresponding pacing channels that selectively functions in a ventricular pacing mode providing ventricular capture verification.

FIG. 3B is yet another embodiment of a functional block diagram for IMD 16. FIG. 3B depicts bipolar RA lead 22, bipolar RV lead 18, and bipolar LV CS lead 20 without the LA CS pace/sense electrodes 28 and 30 coupled with an IPG circuit 31 having programmable modes and parameters of a bi-ventricular DDD/R type known in the pacing art. In turn, the sensor signal processing circuit 49 indirectly couples to the timing circuit 83 and via data and control bus to microcomputer circuitry 33. Optionally, sensor signal process 49 is coupled to another sensor such as an oxygenation sensors, pressure sensors, pH sensors and respiration sensors etc. The IPG circuit 31 is illustrated in a functional block diagram divided generally into a microcomputer circuit 33 and a pacing circuit 83. The pacing circuit includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 320, while battery 29 provides power. Power-on-reset circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 320, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82C in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the atrial-left ventricular pace (A-LVp) delay (or atrial right ventricular pace (A-RVp) delay) from a preceding A-EVENT or A-TRIG, a post-ventricular timer for timing post-ventricular time periods, and a date/time clock 83G.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 83F time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and indifferent electrodes (IND) to the RA pace pulse generator (and LA pace pulse generator if provided), RV pace pulse generator and LV pace pulse generator. Indifferent electrode means any electrode that has no interaction with a designated element. For example there is no interaction between the atrial electrodes and the LV electrode (i.e. no pacing, sensing, or even sub-threshold measurements) since that pathway has no value. If a RV electrode can interact with the LV electrode, then the RV electrode cannot be defined as being indifferent unless specifically defined as isolated from the LV electrode.

Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode on lead 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode on lead 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

A pacing (e.g., for LV and/or BV pacing) ratio or percentage, which is the number of paced heart beats divided by the total number of heart beats, often expressed as a percentage of the total number of heart beats, may be a useful metric for evaluating the effectiveness of CRT but, there are cases in which the pacing ratio or percentage is misleading. For example, in some scenarios such as when pseudo-fusion (e.g., ventricular pacing fails to properly alter electrical activation patterns) is occurring, a high pacing ratio or percentage may not necessarily mean that CRT is effective. Automatic beat-to-beat analysis of the evoked response (e.g., paced QRS complexes) in monitored EGM signals may be used to determine whether the paced heartbeat was effectively paced, and hence, provides more resolution to a pacing ratio. For example, the heartbeats that were paced but determined to not be effectively paced (e.g., depending on the degree of fusion between intrinsic and paced activation, etc.) may be excluded from the pacing ratio thereby providing a more accurate metric of pacing efficacy and/or efficiency, which may referred to as a pacing effectiveness ratio.

A feature-based classification may enable beat-to-beat rhythm classification in a device (e.g., IMD 16) employing cardiac pacing (e.g., CRT pacing such as left ventricular fusion pacing, biventricular pacing (BiV), multisite LV pacing etc.) and may add value to the device by providing useful diagnostic indices to a physician. The computational price involved in such feature-based beat-to-beat classifications may be minimal and may be implemented within the architecture of devices such as the IMD 16 described herein with reference to FIGS. 1-3B. For example, the exemplary methods described herein may combine algebraic operations and comparisons and/or may require a single normalization per beat compared to multiple intensive mathematical operations and normalizations that are often required for detailed template matching algorithms.

Figure 4:
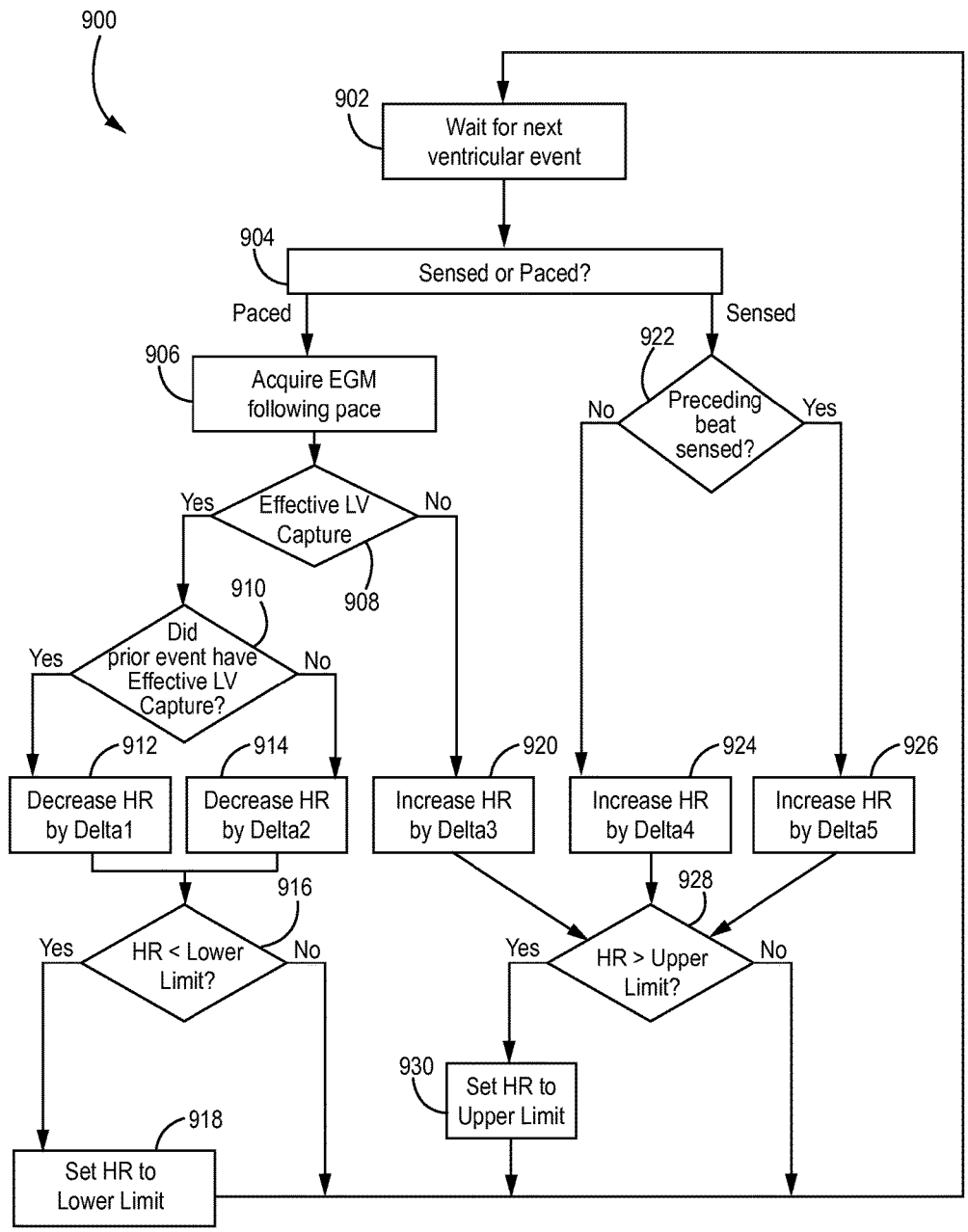
FIG. 4 is a flowchart of an exemplary normal mode employed by an implantable medical device to modulate the biventricular (BiV) pacing rate to increase the percentage of effective BiV capture during atrial fibrillation.
Figure 5:
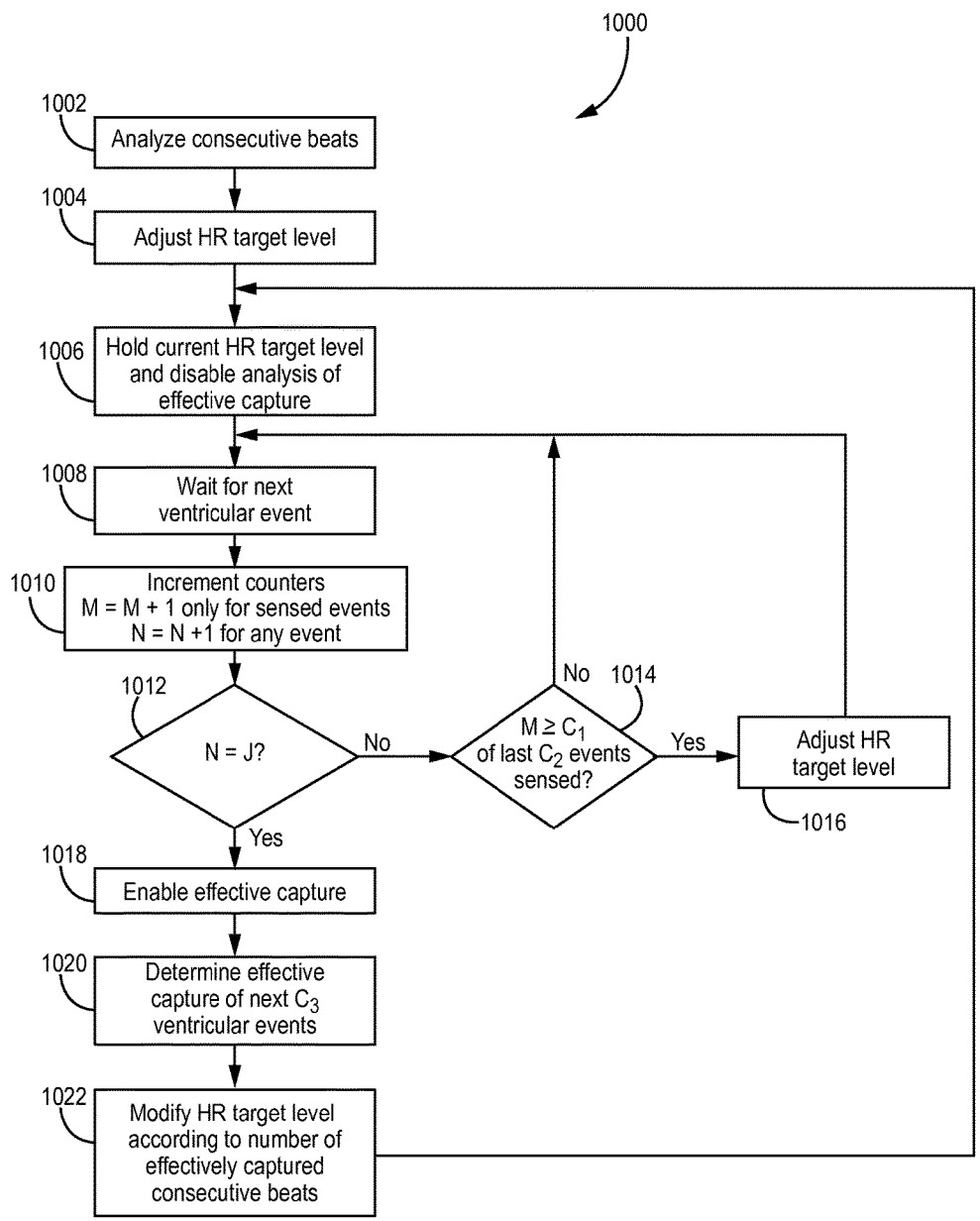
FIG. 5 is a flowchart of an exemplary duty cycle mode employed by an implantable medical device to modulate the BiV pacing rate to increase the percentage of effective BiV capture during atrial fibrillation.

The present disclosure is directed to increasing a patient's percent of effective CRT pacing during AF without significantly increasing ventricular rate. FIG. 4 depicts a normal process mode 900 which is continuously implemented to modify IMD 16 pacing rate during AF. Normal process mode 900 begins at block 902 in which the process 900 waits for the detection of a next ventricular event. At block 904, after the next ventricular event has been detected, a determination is made as to whether the ventricular event was a sensed ventricular event or a paced ventricular event. IMD 16 can automatically determine sensed from paced ventricular events by tracking whether the signal is acquired from an electrode used to sense or pace at a particular time. Paced ventricular events follow the paced path to block 906 in which an EGM is acquired. It can be advantageous for the EGM to be acquired between the LV pacing cathode and a distant (i.e. indifferent) electrode like the RV coil or the device case (i.e. housing electrode 58). Generation of EGM data is described in U.S. Pat. No. 5,776,168 which is incorporated by reference in its entirety. Other methods of obtaining EGM data can also be used.

At decision block 908, the processor 80 uses EGM data to determine whether effective LV capture has occurred in response to the sensed ventricular event. U.S. patent application Ser. No. 13/707,366, filed Dec. 6, 2012 and entitled Effective Capture Test, incorporated by reference in its entirety herein, discloses exemplary processes that rely on the EGM data to determine whether pacing stimulus is effectively capturing a ventricle. Other exemplary processes that can be used to determine effective capture include U.S. Pat. No. 6,044,296. If there is not effective LV capture, the NO path from block 908 continues to block 920 which causes a HR target level to be increased by Delta3. Exemplary values for Delta3 are presented below in Table 1. The HR target level is the desired or ideal HR goal for a patient. If the patient has decreased cardiac capacity, the target HR may not be within a normal HR range.

Block 928, ensures that the HR target level stays within the upper limit programmed into IMD 16. At decision block 928, a determination is then made as to whether the HR is greater than an upper limit. HR is the actual HR sensed by IMD 16 from a patient at a particular time. The upper limit is related to the upper limit of the programmable pacing rate. For a patient, the upper limit can be predetermined or determined by using data dynamically updated from physiological data from the patient. The upper limit can range from about 100 BPM to about 150 BPM. If the HR is greater than an upper limit, the YES path continues to block 930 and the HR target level is then set at the upper limit level. Thereafter, the RETURN path continues to block 902. If the HR is less than or equal to the upper limit, the NO path from block 928 returns to block 902.

Returning to block 908, if the paced ventricular event provides effective LV capture, then the YES path from block 908 continues to decision block 910. At block 910, a determination is made as to whether the prior ventricular event had effective LV capture. The prior ventricular event is defined as the ventricular event that was immediately before the "next ventricular event" from block 902. If the prior ventricular event had also effectively captured the LV, the YES path continues to block 912 in which the HR target level is decreased by Delta1. Exemplary values for Delta1 are listed in Table 1.

If the prior ventricular event did not provide effective LV capture, then the NO path from block 910 decreases the HR target level by Delta2 at block 914. Exemplary values for Delta2 is presented below in Table 1.

Block 916, like block 928, ensures that the HR stays within the programmed limits into IMD 16. In particular, a determination is made as to whether the HR is lower than the lower limit at decision block 916. Generally, the lower limit is set to the sensor rate (i.e., the HR determined by the activity sensor in rate-responsive pacing modes). Alternatively, the lower limit could be set to the programmed lower rate limit of the IMD 16. The programmed lower rate limit is typically set to 40-70 BPM. The lower rate can also be impacted by "sleep mode" as described in the art. Sleep mode for IMD 16 can be configured to drop the lower rate at night.

If the HR is below the lower limit, then the HR target level is set to the lower limit at block 918. If the HR is equal to or above the lower limit, then the HR target level remains unchanged and the NO path from block 916 returns to block 902 to wait for the next ventricular event.

Returning to block 904, if a sensed ventricular event has occurred rather than a paced ventricular event, then a determination is made at decision block 922 as to whether the preceding beat was sensed. If the preceding beat was not sensed, the NO path from decision block 922 requires that the HR target level be increased by Delta4 at block 924. If the preceding beat was sensed, the YES path from decision block 922 requires that the HR target level be increased by Delta5 at block 926. The logic of block 928, previously explained, determines whether the sensed ventricular event has the HR target level set to the upper limit or the RETURN path to block 902 is followed.

In the exemplary table presented below, the "Deltas" refer to the above flow diagram for the normal operation mode 900. The Deltas are functions of heart rate thereby allowing the algorithm to become less "aggressive" at higher heart rates. As previously explained, the heart rate, at the end of the initialization period, is augmented by a Delta value. The Delta value selected from Table 1 depends upon the patient's heart rate determined by IMD 16. IMD 16 ensures that the HR is analyzed for a sufficient period of time to achieve a relatively consistent reading of the HR during real-time. The HR is then used to determine the appropriate Delta to adjust the HR target level.

Deltas1 and 2 involve decreases to the HR target level while Deltas 3, 4, and 5 involve increases to the HR target level.

TABLE 1 exemplary Delta values

HR change as a function of HR

| Delta values | HR > 90 BPM | HR in a range between 70 BPM to 90 BPM | HR < 70 BPM |
| --- | --- | --- | --- |
| Delta1 (BPM) | 1 | 2 | 2 |
| Delta2 (BPM) | 0.5 | 0.5 | 1 |
| Delta3 (BPM) | 1 | 2 | 3 |
| Delta4 (BPM) | 1 | 2 | 3 |
| Delta5 (BPM) | 1 | 3 | 5 |

While values for each Delta is found in the table, it is generally understood that other values may also be used. In one or more embodiments, the ratios between each Delta can be useful in determining the HR target level.

Figure 6:
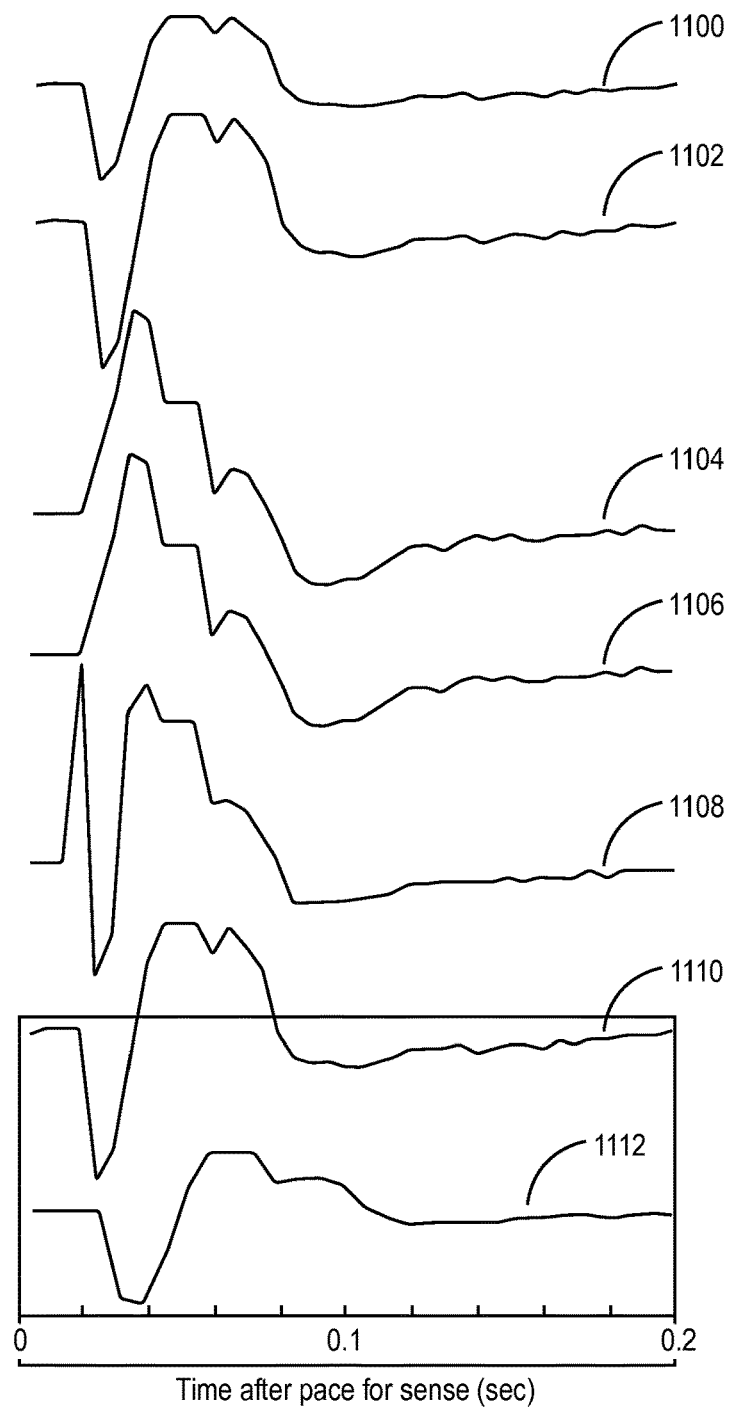
FIG. 6 depicts an exemplary set of sequential beat signals that may occur during a normal mode of operation.

FIG. 6 depicts an exemplary set of sequential beat signals that may occur during a normal mode of operation described in the flow diagram of FIG. 4. The sequential beats show differences in the evoked responses following delivery of a pace or the intrinsic activation following a sensing of a ventricular event, as observed in the electrogram sensed between the LV pacing cathode and an indifferent electrode like the RV coil or device case. The Y-axis depicts the amplitude while the X-axis depicts the time, measured in seconds, after delivering a pacing stimulus or sensing a ventricular event. Signals 1100 and 1102 are indicative of pacing stimulus that effectively captures a ventricle. The observation of two consecutively effective capture beats results in an decrease in the HR target level by Delta1. Signal 1104 is indicative of a sensed ventricular event. Observation of a sensed ventricular event that is preceded by an effective capture event results in an increase in the HR target level by Delta4. Signal 1106 is indicative of a sensed ventricular event. Observation of two consecutively sensed events results in an increase in the HR target level by Delta5. Signal 1108 is indicative of a paced ventricular event with ineffective capture, which results in an increase in the HR target level by Delta3. Signal 1110 is indicative of a paced ventricular event with effective capture. Signal 1110 resulted in a decrease in the HR target level by Delta2. Signal 1112 is indicative of a paced ventricular event with effective capture. This resulted in a decrease in the HR target level by Delta1.

While FIGS. 4 and 6 relate to normal process mode, a duty cycle mode that conserves battery life may also be used to modulate the pacing rate in response to observation of effective capture during AF. Duty cycle mode means that the IMD 16 is not continuously verifying whether effective capture of a ventricle is occurring during AF. Specifically, duty cycle mode means that verification of effective capture during AF only occurs a certain percentage of the time. For example, the duty cycle mode may operate 10% percent of the time (e.g. minutes, hours, daily, weekly, etc.). Alternatively, the duty-cycle mode of operation can be configured as a function of AF burden. For example, the duty cycle mode can operate a certain number of hours while AF is detected. In one or more embodiments, duty cycle mode can be configured as a function of beat numbers (i.e., 10 beats out of 40) or seconds (i.e., 10 seconds out of 40 seconds).

In yet another embodiment, a combination of the normal mode of operation and the duty cycle mode of operation can be employed. A normal mode of operation can be used for the first N hours of AF per day where N is any number between 1 and 12 followed by a duty-cycle mode. A fixed or adjustable duty-cycle mode of X % can be then employed by the IMD. The duty-cycle mode of X % means that the feature, related to determining effective capture during AF, is activated in the duty cycle mode such that some beats are actively monitored every minute or every 30 seconds (e.g. 10 beats of every 40 beats, 10 beats of every 30 beats etc.). In one or more embodiments, the feature, related to modulating the pacing rate in response to observation of effective capture during AF, is not turned off several minutes at a time.

In yet another embodiment, the first day IMD 16 operates in the normal mode (i.e. continuously "on" or activated) for a day or more and then switches to fixed or adjustable dual cycle mode. Fixed dual cycle time means that the operation that determines effective capture during AF occurs over a consistent amount of time.

In still yet another embodiment, the duty cycle mode can operate a predetermined percentage of time over each hour. For example, the duty cycle mode can operate 50% of an hour; therefore, the duty cycle mode would run, for example, a certain number of beats and then off for a certain number of beats. More specifically, a 50% duty cycle mode is executed as 10 beats on, 10 beats off and not 30 minutes on and 30 minutes off.

Operations of duty cycle mode are similar to the normal cycle mode except as modified therein. Process 1000 of FIG. 5 begins at block 1002 in which a predetermined amount of consecutive beats (e.g. 30 beats etc.) are analyzed. Based upon the analysis, the HR target level can be adjusted according to the flow diagram of FIG. 4 which outlines the operation for the normal operation mode. For example, the HR target level is increased by 1 BPM if the patient's detected HR is greater than 100 BPM. In one or more other embodiments, the HR target level is increased by +2 BPM if the patient's HR is determined to be between 80 BPM and 100 BPM. At block 1004, the final HR target level can be increased by determining application of the conditions below. For example, the HR target level can be increased by a predetermined amount such as "1" if the beats per minute (BPM) is greater than 100 BPM. Alternatively, the HR target level can be increased by another predetermined amount such as "3" if the BPM is greater than 80 BPM but less than 100 BPM. In yet another embodiment, the HR target level can be increased by yet another predetermined amount such as "5" if the BPM) is greater than 100 BPM. Table 2 summarizes the BPM target level based upon the presently or latest sensed BPM from the patient. Table 2 applies to adjustments made to the HR target level at block 1004.

TABLE 2

Increase BPM target level based upon the presently or latest sensed BPM

| HR detected in patient | Adjustment to BPM target level | Exemplary adjustment to BPM target level |
| --- | --- | --- |
| HR > 100 BPM | X | X = 1 |
| 80 < HR < 100 | X + 2 | 3 |
| HR < 80 BPM | X + 4 | 5 |

Block 1006 represents a number of operations. For example, the current HR target level is set to the current or latest HR target level value stored in memory. Additionally, the analysis of effective capture is disabled to allow the HR target level to be increased until the ventricular event counter equals a predetermined integer J. By checking a predetermined number of ventricular events, the data obtained as the result of the ventricular events ensures greater consistency in the data. In one or more embodiments, integer J can be any integer such as 30 or less. In one or more other embodiments, J can be set to 20 or less. In yet another embodiment, J=10 or less. In addition to setting the value of integer J, the sensed ventricular event counter, M, can also be set to a predetermined value (e.g. 0, 1 etc.).

At block 1008, process 1000 waits for the next ventricular event to be sensed. After the next ventricular event has been sensed, the total ventricular events (i.e. sensed and paced), represented by N, is incremented at block 1010. M, the counter representing sensed ventricular events (i.e. not paced ventricular events), is only incremented when a sensed event is detected at block 1010.

At block 1012, a determination is made as to whether a ventricular event counter is equal to a predetermined integer J. J is the total number of ventricular events to be counted. If a ventricular event counter is not equal to a predetermined integer J, the NO path from block 1012 continues to decision block 1014. Block 1014 determines whether the pacing pulse is effectively capturing the ventricle(s) by comparing the sensed ventricular beats to a predetermined integer referred to as C1 (e.g. 2, 4, or 6, etc.). If M is greater than or equal to C1, then the HR target level the YES path from block 1014 continues to block 1016 in which the HR target level is increased by 2 BPM. The NO path from block 1014 returns to block 1008 to wait for the next ventricular event.

The YES path from block 1012 continues to block 1018 in which effective capture analysis is enabled. Effective capture analysis can be performed on any or all EGM data stored into memory. At decision block 1020, a determination is made as to whether effective capture is occurring with the next predetermined number C3 (e.g. 10 etc.) ventricular events. At block 1022, the HR target level is modified according to the number of effectively captured consecutive beats (e.g. 5-10). For example, if the number of effectively captured beats is less than 3 beats out of 10 then, the HR target level is increased by +3 BPM. In another example, if the number of effectively captured beats is between 3 and 6 beats (i.e. 3<beats<6) out of 10 beats, then the HR target level is increased by +2 BPM. In yet another example, if the beats equal 6 or 7 out of 10 beats, then the HR target level is increased by +1 BPM. In yet another example, if the effectively captured beats equal 8 out of 10 beat, the HR target level remains unchanged. In still yet another example, if the effectively captured beats equal 9 out of 10 beats, then the HR target level is decreased by −2 BPM. In yet another example, if the number effectively captured beats is 10 out of 10 beats, then the HR target level is decreased by −3 BPM.

In one or more preferred embodiments, a non-duty cycle mode is used for the first 30 seconds (i.e., an "initialization period") to adjust the heart rate during AF. The heart rate at the end of the initialization period is then augmented by 1 BPM if the heart rate is greater than 100 BPM, 3 BPM if the heart rate is greater than 80 BPM but less than 100 BPM, and 5 BPM if the heart rate is less than 80 BPM. This final designated pacing rate is then applied during a hold period of 30 seconds. During the hold period, the pacing rate can only be adjusted upward if 6 of 10 ventricular events in any period of 10 ventricular events are sensed, not paced. If this occurs, the heart rate is increased by 2 BPM and the buffer of 10 beats is cleared. Battery power is conserved because determination of sensed versus paced is very simple compared to the determination of effective capture versus ineffective capture. At the end of the hold period, 10 beats are analyzed for effective capture. Depending on how many of the 10 beats have effective capture, the pacing rate for the next 30 second hold period is adjusted up or down.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Listed below are co-pending U.S. patent applications that describe various aspects of the apparatus and methods described herein. The co-pending applications are incorporated by reference in their entireties.

Co-pending U.S. patent application Ser. No. 13/707,366 entitled "EFFECTIVE CAPTURE" filed by Subham Ghosh et al. and assigned to the same assignee of the present disclosure.

Co-pending U.S. patent application Ser. No. 13/707,391 entitled "EFFECTIVE CAPTURE" filed by Subham Ghosh et al. and assigned to the same assignee of the present disclosure.

Co-pending U.S. patent application Ser. No. 13/707,440 entitled "EFFECTIVE CAPTURE" filed by Subham Ghosh et al. and assigned to the same assignee of the present disclosure.

Co-pending U.S. patent application Ser. No. 13/707,458 entitled "EFFECTIVE CAPTURE" filed by Subham Ghosh et al. and assigned to the same assignee of the present disclosure.

Co-pending U.S. patent application Ser. No. 13/772,840 entitled "CRITERIA FOR OPTIMAL ELECTRICAL RESYNCHRONIZATION DURING FUSION PACING" filed by Subham Ghosh et al. and assigned to the same assignee of the present disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. An apparatus for determining whether a ventricular pacing stimulus is capturing a paced ventricle during atrial fibrillation, comprising:
    processing means for determining whether a patient is experiencing atrial fibrillation;
    delivering means for delivering the ventricular pacing stimulus in response to determining the patient is in atrial fibrillation;
    sensing means for sensing a signal in response to the ventricular pacing stimulus;
    processing means for determining whether the ventricular pacing stimulus is effectively capturing the paced ventricle;
    modifying means for modifying a pacing rate during atrial fibrillation in response to the determination of effective capture; and
    increasing a percentage of effective ventricular capture during atrial fibrillation responsive to modifying the pacing rate during atrial fibrillation.

2. The apparatus of claim 1 wherein the processing means for determining whether the ventricular pacing stimulus is capturing the paced ventricle is periodically performed to maximize battery life.

3. The apparatus of claim 2 wherein periodically determining whether the ventricular pacing stimulus is capturing the paced ventricle occurs solely during atrial fibrillation.

4. The apparatus of claim 1 wherein the ventricular pacing stimulus is left ventricular (LV) occurring at a LV tip electrode, and a monitoring vector is selected from one of a Lvtip-Rvcoil or a Lvtip-device case.

5. The apparatus of claim 1 wherein LV pacing is occurring at the LV ring, and a monitoring vector is selected from one of a LVring-Rvcoil or a LVring-device case.

6. The apparatus of claim 1 wherein LV pacing occurs at a third LV electrode, and a monitoring vector is selected from one of the third LVelectrode-Rvcoil or third LVelectrode-device case.

7. The apparatus of claim 1 wherein LV pacing is occurring at a fourth LV electrode, and a monitoring vector is selected from one of the fourth LVelectrode-Rvcoil or fourth LVelectrode-device case.

8. The apparatus of claim 1 wherein determining whether a ventricular pacing stimulus is capturing a paced ventricle occurs during normal device pace timing operation.

9. The apparatus of claim 1 wherein a duty cycle mode is employed when determining whether effective capture during AF.

10. The apparatus of claim 1 determining whether a ventricular event is a paced ventricular event.

11. The apparatus of claim 10 further comprising acquiring an EGM in response to determining ventricular event is a paced ventricular event.

12. The apparatus of claim 1 further comprising:
determining whether a prior ventricular event provided effective capture.

13. The apparatus of claim 12 further comprising:
decreasing a heart rate (HR) target level by Delta1 in response to determining the prior ventricular event effectively captured the ventricle.

14. The apparatus of claim 12 further comprising:
decreasing a HR target level by Delta2 in response to determining the prior ventricular event did not effectively capture the ventricle.

15. The apparatus of claim 1 further comprising:
increasing a HR target level by Delta3 in response to determining the ventricle was not captured by the ventricular pacing stimulus.

16. The apparatus of claim 15 further comprising:
determining whether the heart rate exceeds an upper limit; and
setting the HR target level to the upper limit if the heart rate exceeds the upper limit.

17. The apparatus of claim 1 further comprising:
adjusting a heart rate target level in response to determining a plurality of effectively captured beats.

18. The apparatus of claim 17 wherein the heart rate target level is increased up to three beats per minute to a heart rate value in response to determining less than three out of ten beats were effectively captured.

19. The apparatus of claim 17 wherein the heart rate target level is increased up to two beats per minute to a heart rate value in response to determining less than six beats and greater than three out of ten beats were effectively captured.

20. The apparatus of claim 17 wherein the heart rate target level is increased by one beat per minute to a heart rate value in response to determining six or seven beats out of ten beats were effectively captured.

21. The apparatus of claim 17 wherein the heart rate target level is decreased by one to two beats per minute to a heart rate value in response to determining nine beats out of ten beats were effectively captured.

22. The apparatus of claim 17 wherein the heart rate target level is decreased by three beats per minute to a heart rate value in response to determining ten beats out of ten beats were effectively captured.

23. The apparatus of claim 1 wherein the ventricular pacing stimulus is delivered during one of biventricular pacing, multisite left ventricular pacing and fusion pacing.

24. A method for determining whether a ventricular pacing stimulus is capturing a paced ventricle during atrial fibrillation, comprising:
determining whether a patient is experiencing atrial fibrillation;
delivering the ventricular pacing stimulus in response to determining the patient is in atrial fibrillation;
sensing a signal in response to the ventricular pacing stimulus;
determining whether the ventricular pacing stimulus is effectively capturing the paced ventricle;
modifying a pacing rate during atrial fibrillation in response to the determination of effective capture; and
increasing a percentage of effective ventricular capture during atrial fibrillation responsive to modifying the pacing rate during atrial fibrillation.

25. A method of claim 24 wherein determining whether the ventricular pacing stimulus is capturing the paced ventricle is periodically performed to maximize battery life.

26. A method of claim 24 wherein periodically determining whether the ventricular pacing stimulus is capturing the paced ventricle occurs solely during atrial fibrillation.

* * * * *